US011642516B2

United States Patent
Várkuti

(10) Patent No.: US 11,642,516 B2
(45) Date of Patent: May 9, 2023

(54) NEURONAL SIGNAL SYSTEM FOR BEHAVIOR MODIFICATION

(71) Applicant: CereGate GmbH, Munich (DE)

(72) Inventor: Bálint Várkuti, Munich (DE)

(73) Assignee: CEREGATE GMBH, Munich (DE)

( * ) Notice: Subject to any disclaimer, the term of this patent is extended or adjusted under 35 U.S.C. 154(b) by 486 days.

(21) Appl. No.: 16/517,112

(22) Filed: Jul. 19, 2019

(65) Prior Publication Data

US 2020/0398046 A1    Dec. 24, 2020

(30) Foreign Application Priority Data

Jun. 24, 2019    (DE) .................... 10 2019 209 096.6

(51) Int. Cl.
*A61N 1/05*    (2006.01)
*A61N 1/36*    (2006.01)
(Continued)

(52) U.S. Cl.
CPC .......... *A61N 1/0531* (2013.01); *A61N 1/0534* (2013.01); *A61N 1/36082* (2013.01);
(Continued)

(58) Field of Classification Search
CPC ................ A61N 1/0531; A61N 1/0534; A61N 1/36082; A61N 1/36139; A61N 1/36064;
(Continued)

(56) References Cited

U.S. PATENT DOCUMENTS

| 4,441,202 A | 4/1984 | Tong et al. |
| 4,445,512 A | 5/1984 | Krupka et al. |

(Continued)

FOREIGN PATENT DOCUMENTS

| DE | 102019202666 A1 | 8/2020 |
| DE | 102019209096 A1 | 12/2020 |

(Continued)

OTHER PUBLICATIONS

First Office Action dated Mar. 17, 2020 for German Application No. DE102019209096.6, 8 pages.
(Continued)

*Primary Examiner* — Aaron F Roane
(74) *Attorney, Agent, or Firm* — Kowert, Hood, Munyon, Rankin & Goetzel, P.C.

(57) ABSTRACT

Systems and methods for stimulating the sensory cortex of an individual by obtaining a neuronal stimulation signal adapted to provide a movement cue for the individual and transmitting the neuronal stimulation signal to an electric contact of a neuronal stimulation electrode that is already implanted into the brain of the individual for a purpose different from providing the movement cue. Proprioceptive information is communicated to the individual by obtaining information about the body posture of the individual and applying a neuronal stimulation signal to an afferent axon targeting a sensory neuron in the cortex of the individual. The neuronal stimulation signal is determined based on the obtained body posture information and corresponds to the proprioceptive information. A first neuronal stimulation signal providing the movement cue and a second neuronal stimulation signal providing the proprioceptive information may be applied together to the cortex of the individual.

36 Claims, 8 Drawing Sheets

Figure 1:
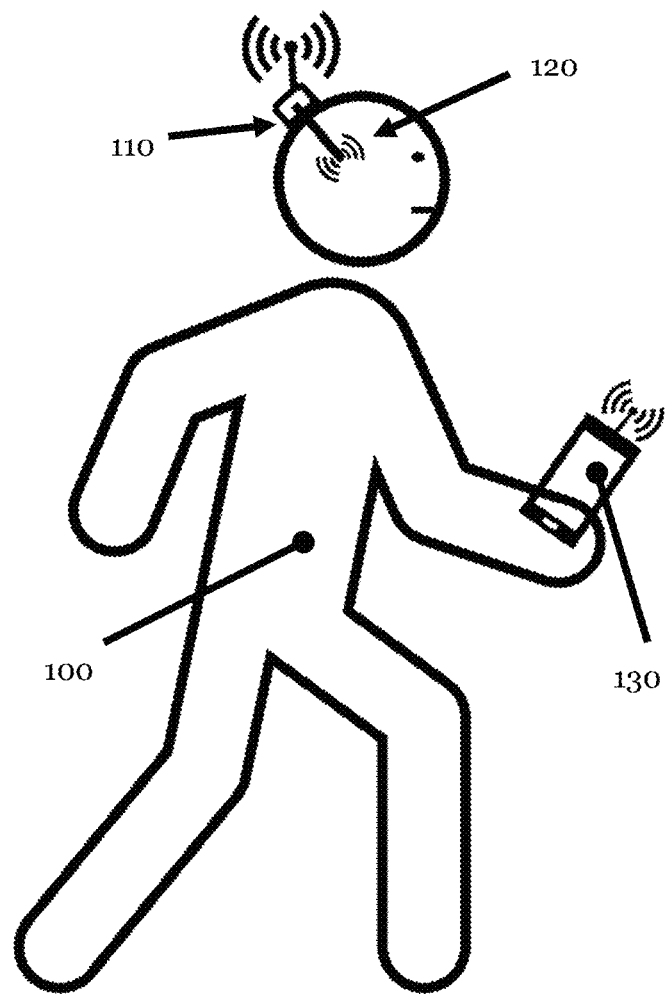

(51) Int. Cl.
   *A61N 1/372* (2006.01)
   *A61N 1/378* (2006.01)
(52) U.S. Cl.
   CPC ...... *A61N 1/36139* (2013.01); *A61N 1/36064* (2013.01); *A61N 1/36067* (2013.01); *A61N 1/3787* (2013.01); *A61N 1/37288* (2013.01)
(58) Field of Classification Search
   CPC ............ A61N 1/36067; A61N 1/37288; A61N 1/3787
   USPC .......................................................... 607/45
   See application file for complete search history.

(56) References Cited

U.S. PATENT DOCUMENTS

| | | |
|---|---|---|
| 4,488,555 A | 12/1984 | Imran |
| 5,800,535 A | 9/1998 | Howard, III |
| 6,400,989 B1 | 6/2002 | Eckmiller |
| 7,751,884 B2 | 7/2010 | Ternes et al. |
| 7,774,056 B2 | 8/2010 | Torgerson |
| 8,193,766 B2 | 6/2012 | Rondoni et al. |
| 8,290,596 B2 | 10/2012 | Wei et al. |
| 8,352,029 B2 | 1/2013 | Ternes et al. |
| 8,364,271 B2 | 1/2013 | De Ridder |
| 8,380,314 B2 | 2/2013 | Panken et al. |
| 8,423,145 B2 | 4/2013 | Pless et al. |
| 8,437,858 B2 | 5/2013 | Dapper et al. |
| 8,475,172 B2 | 7/2013 | Lieberman et al. |
| 8,494,633 B2 | 7/2013 | Tobacman |
| 8,509,904 B2 | 8/2013 | Rickert et al. |
| 8,812,128 B2 | 8/2014 | Kothandaraman |
| 9,095,314 B2 | 8/2015 | Osorio et al. |
| 9,314,190 B1 | 4/2016 | Giuffrida et al. |
| 9,357,938 B2 | 6/2016 | Ang et al. |
| 9,526,896 B2 | 12/2016 | Greenberg et al. |
| 9,636,497 B2 | 5/2017 | Bradley et al. |
| 9,713,720 B2 | 7/2017 | Zhu |
| 9,974,478 B1 | 5/2018 | Brokaw et al. |
| 10,568,559 B2 | 2/2020 | Parker et al. |
| 2003/0065366 A1 | 4/2003 | Merritt et al. |
| 2006/0129205 A1 | 6/2006 | Boveja et al. |
| 2006/0241717 A1 | 10/2006 | Whitehurst et al. |
| 2006/0241718 A1 | 10/2006 | Tyler et al. |
| 2007/0027397 A1 | 2/2007 | Fischell et al. |
| 2007/0250134 A1 | 10/2007 | Miesel et al. |
| 2008/0129517 A1 | 6/2008 | Crosby et al. |
| 2008/0139954 A1 | 6/2008 | Day et al. |
| 2009/0264789 A1 | 10/2009 | Molnar et al. |
| 2009/0306741 A1 | 12/2009 | Hogle et al. |
| 2010/0057161 A1 | 3/2010 | Machado et al. |
| 2010/0094382 A1 | 4/2010 | Pezaris et al. |
| 2010/0249879 A1 | 9/2010 | Bracker et al. |
| 2013/0150914 A1 | 6/2013 | Kelly et al. |
| 2013/0253299 A1 | 9/2013 | Weber et al. |
| 2014/0081348 A1 | 3/2014 | Fischell |
| 2014/0379046 A1 | 12/2014 | Tcheng et al. |
| 2015/0018724 A1 | 1/2015 | Hsu et al. |
| 2015/0073492 A1 | 3/2015 | Kilgard et al. |
| 2015/0290453 A1 | 10/2015 | Tyler et al. |
| 2016/0022992 A1 | 1/2016 | Franke et al. |
| 2016/0121118 A1 | 5/2016 | Franke et al. |
| 2017/0182328 A1 | 6/2017 | Moffitt |
| 2018/0050198 A1 | 2/2018 | Mazanec et al. |
| 2019/0030338 A1 | 1/2019 | Wu et al. |
| 2020/0269049 A1 | 8/2020 | Varkuti |

FOREIGN PATENT DOCUMENTS

| | | | |
|---|---|---|---|
| EP | 2552304 B1 | 9/2015 | |
| EP | 3229893 A1 | 10/2017 | |
| EP | 3431138 A1 | 1/2019 | |
| EP | 2486897 B1 | 5/2019 | |
| KR | 20170132055 | 12/2017 | |
| KR | 101841625 B1 | 5/2018 | |
| WO | 2012003451 A2 | 1/2012 | |
| WO | 2012003451 A3 | 1/2012 | |
| WO | 2016116397 A1 | 7/2016 | |
| WO | 2018057667 A1 | 3/2018 | |
| WO | 2018109715 A1 | 6/2018 | |
| WO | WO 2018/109715 | * 6/2018 | .............. A61N 1/05 |
| WO | 2020174051 A1 | 9/2020 | |

OTHER PUBLICATIONS

Heming E., et al., "Designing a Somatosensory Neural Prosthesis: Percepts Evoked by Different Patterns of Thalamic Stimulation," Journal of Neural Engineering, Dec. 1, 2010, vol. 7 (6), 7 pages.
International Preliminary Report issued in International Application No. PCT/EP2020/055156, dated Sep. 10, 2021, 17 pages.
International Search report and Written Opinion issued in International Application No. PCT/EP2020/055156, dated Jul. 21, 2020, 22 pages.
Office Action for European Application No. 20200707624, dated Dec. 7, 2021, 14 pages.
First Office Action dated Oct. 16, 2019 for German Application No. DE 10 2019 202 666.4, 14 pgs.
Beauchamp et al., "Dynamic Electrical Stimulation of Sites in Visual Cortex Produces Form Vision in Sighted and Blind Humans," bioRxiv preprint, http://dx.doi.org/10.1101/462697, Nov. 5, 2018, 24 pgs.
Lee et al., "Engineering Artificial Somatosensation Through Cortical Stimulation in Humans," Frontiers in Systems Neuroscience, www.frontiersin.org, Jun. 4, 2018, vol. 12, Article 24, 11 pgs.
Roelfsema et al., "Mind Reading and Writing: The Future of Neurotechnology," Trends in Cognitive Sciences, https://doi.org/10.1016/j.tics.2018.04.001, May 6, 2018, Elsevier Ltd., 14 pgs.
Anderson et al., "Optimized Programming Algorithm for Cylindrical and Directional Deep Brain Stimulation Electrodes," https://doi.org/10.1088/1741-2552/aaa14b, Journal of Neural Engineering, Jan. 24, 2018, IOP Publishing Ltd., 19 pgs.
"Swan et al., ""Sensory Percepts Induced by Microwire Array and DBS Microstimulation in Human Sensory Thalamus,"" https://doi.org/10.1016/j.brs.2017 .10.017, Brain Stimulation 11 (2018) 416-422, Elsevier Inc."
Yadav, A.P., Li, D. & Nicolelis, M.A.L.: "A Brain to Spine Interface for Transferring Artificial Sensory Information". Sci Rep 10, 900 (2020),15 pgs.
"Sensory Electrical Stimulation Cueing May Reduce Freezingof Gait Episodes in Parkinson's Disease"; L. Rosenthal et. al.; Hindawi Journal of Healthcare Engineering; 2018, Article ID 4684925, 6 pgs.
"Effect of rhythmic auditory cueingon parkinsonian gait: A systematic review and meta-analysis"; S. Ghai et al.; Nature Scientic Reports; (2018) 8:506; DOI:10.1038/s41598-017-16232-5, 19 pgs.
Examination Report for German Application No. 1020192014752.6, dated Apr. 16, 2021, 5 pgs.
Donati, A., Shokur, S., Morya, E. et al. "Long-Term Training with a Brain-Machine Interface-Based Gait Protocol Induces Partial Neurological Recovery in Paraplegic Patients" Sci Rep 6, 30383 (2016); https://doi.org/10.1038/srep30383, 16 pgs.
Examination Report for German Application No. 1020192014752.6, dated Jun. 16, 2020, 8 pgs.
Invitation to Pay Additional Fees and, Where Applicable, Protest Fee and Partial International Search for PCT/EP2020/055156, dated May 29, 2020, 21 pgs.
Heming E A et al: "Designing a Thalamic Somatosensory Neural Prosthesis: Consistency and Persistence of Percepts Evoked by Electrical Stimulation", IEEE Transactions on Neural Systems and Rehabilitationengineering, IEEE Service Center, New York, NY, US, vol. 19, No. 5, Oct. 1, 2011 (Oct. 1, 2011), pp. 477-482.

* cited by examiner

NEURONAL SIGNAL SYSTEM FOR BEHAVIOR MODIFICATION

1. TECHNICAL FIELD

The present invention relates to signal and data processing systems for providing neuronal stimulation signals to an individual that may be used for behavior and, in particular, movement modification.

2. TECHNICAL BACKGROUND

The present application is directed to neuronal stimulation systems for behavior and movement modification, in particular, in the context of the treatment of neurological movement impairments.

Neurological diseases such as Parkinson's disease (PD), essential tremor or dystonia may severely degrade the movement and coordination abilities of affected patients. It is well known, that certain symptoms of such diseases can be successfully treated or at least ameliorated via stimulation of the nervous system of the affected patients.

For instance, deep brain stimulation (DBS) systems send electrical impulses, through implanted electrodes, to specific areas/nuclei of the brain to treat such symptoms. Conventionally, in the treatment of PD symptoms, these nuclei may include the globus pallidus interna, the thalamus and/or the subthalamic nucleus. It is known that DBS of the globus pallidus interna improves motor function while DBS of the thalamus improves tremor but has little effect on bradykinesia or rigidity. Further, DBS of the subthalamic nucleus is associated with reduction in PD medication.

US 2007/0250134 A1 relates to an implantable medical device for delivering different electrical stimulation therapies to the nervous system of a patient in order to suppress different symptoms of PD. One such electrical stimulation therapy is configured to suppress the so called freezing of gait (FOG) symptom while another such electrical stimulation therapy is configured to suppress other PD symptoms such as tremor, bradykinesia or rigidity. At any given time, the medical device delivers the electrical stimulation therapy according to a current set of therapy parameters. The therapy parameters may change over time. The medical device, or another device, periodically determines an activity level of the patient, and associates each determined activity level with the current therapy parameter set. In addition to recording FOG events and determining activity metric values based on such events, the medical device may also control delivery of a stimulus to terminate FOG. For example, if stimulation leads are implanted proximate to the spinal cord or peripheral nerves of the patient the medical device may control delivery of a stimulation perceivable by the patient to prompt the patient to walk, thereby terminating FOG. The stimulation may be rhythmic, e.g., may approximate the rhythm of walking, which may prompt the patient to walk and thereby terminate the FOG.

The recent publication "*Sensory Electrical Stimulation Cueing May Reduce Freezing of Gait Episodes in Parkinson's Disease*"; L. Rosenthal et. al.; Hindawi Journal of Healthcare Engineering; 2018, Article ID 4684925 describes how skin surface electrodes can be used to provide a fixed rhythmic sensory electrical stimulation signal to PD patients in order to reduce the time taken to complete a walking task and to reduce the number of FOG episodes occurring when performing the task.

A different approach for treatment of movement impairments consists in rhythmic auditory cueing. The recent review article "*Effect of rhythmic auditory cueing on parkinsonian gait: A systematic review and meta-analysis*"; S. Ghai et al.; NATURE SCIENTIC REPORTS; (2018) 8:506; DOI:10.1038/s41598-017-16232-5 provides a systematic overview on using rhythmic auditory cueing to enhance gait performance in PD patients.

Moreover, US 2019/0030338 A1 relates to an implantable medical device that is capable of determining whether a patient is susceptible to FOG events during ambulatory movement without the patient actually demonstrating an episode of FOG. The implantable medical device senses, via one or more electrodes, a bioelectrical signal of a brain of the patient while the patient performs a movement associated with FOG. The implantable medical device then determines, based on the sensed bioelectrical signal, whether the patient is susceptible to FOG while the patient is not experiencing an episode of FOG. Further, upon detecting the movement associated with FOG, the implantable medical device delivers an electrical stimulation therapy via a DBS electrode to the patient configured to suppress FOG.

However, the electrical stimulation systems known from the prior art have various deficiencies. For instance, auditory cueing treatment for patients suffering from a movement impairment may degrade the listening capabilities of the patient and distract him from other relevant sounds providing crucial information on his environment.

Further, providing electrical stimulation signals via skin surface electrodes requires bulky electronic equipment to be carried by the patient as well as continuous maintenance of the skin surface electrodes that may degrade and/or detach from the skin due to external moisture or body moisture.

Moreover, conventional DBS systems can only be used to provide unspecific neuromodulation signals that for instance are configured to suppress FOG events or tremor. However, such systems completely lack the capability of continuously enhancing the movement of the patient after a FOG event has been suppressed in terms of regularity, balance and/or body posture.

It is thus the problem of the present invention to provide novel neuronal stimulation systems that improve the known systems such that the above outlined disadvantages of the prior art are at least partially overcome.

3. SUMMARY OF THE INVENTION

The above-mentioned problem is at least partly solved by the subject matter of the independent claims of the present application. Exemplary embodiments of the invention are the subject of the depended claims.

In one embodiment, the present invention provides a system for stimulating the sensory cortex of an individual, comprising: means for obtaining a neuronal stimulation signal adapted to provide a movement cue for the individual and means for transmitting the neuronal stimulation signal to an electric contact of a neuronal stimulation electrode that is implanted into the brain of the individual.

For example, the neuronal stimulation electrode may already be implanted into the brain of the individual for a purpose different from providing the movement cue.

In this manner, no additional electrode has to be implanted but an existing one can be used for interfacing the system provided by the present invention.

For instance, the neuronal stimulation signal may be adapted to elicit a sensory percept, preferably conscious, in the cortex of the individual. The sensory percept may for example be elicited in in at least on of: a somatosensory cortex area; a visual cortex area and an auditory cortex area.

By using such a system, sensory percepts can directly be elicited in the cortex of an individual without stimulation of the sensory organs and or the peripheral nervous system.

For instance, the system provided by the present invention can be interfaced with a DBS electrode that is already implanted into the brain of an individual for the purpose to stimulate the thalamus or the sub-thalamic nucleus with a neuromodulation signal (e.g. for treatment of PD symptoms such as tremor). In this way, the provided system can provide the movement cue via stimulating afferent sensory axons that run in the vicinity of the thalamus and project into the sensory cortex of the brain. Such a system thus allows to provide various types of movement cues directly to the cortex without requiring additional sensory stimulation equipment such as earphones, skin surface contacts, dedicated neuronal stimulation electrodes etc. but makes use of electric contacts that are already available in the vicinity of such afferent sensory axons.

In other words, patients that have already been implanted with a neuronal stimulation electrode for a different purpose can easily also be provided with movement cues via interfacing their already present implant with the neuronal stimulation systems provided by the present invention without undergoing additional surgical procedures or requiring to carry additional equipment.

In some embodiments, the neuronal stimulation electrode may be implanted for the purpose of at least one of: deep brain stimulation; neuronal sensing; an open-loop or closed-loop combination of deep brain stimulation and neuronal sensing; treatment of Parkinson's disease, of epilepsy, dystonia and/or of tremor as well as neuronal communication.

Further, in some embodiments, the electric contact to which the neuronal stimulation signal is transmitted to may not be used for the purpose that is different from providing the movement cue. For instance, if a multi-contact DBS electrode is used for the purpose of applying a neuromodulation therapy such as a treatment of PD symptoms typically only a subset of its electric contacts (e.g. one contact) is actually used for applying the neuromodulation therapy stimulation signal. The remaining unused contacts can thus be used to stimulate afferent sensory axons targeting the sensory cortex of the individual and thereby to provide a sensory movement cue or other movement information to the patient.

Alternatively, an electric contact that is used for applying the neuromodulation therapy can also be used in an alternating manner. For instance, the movement cue may be provided during periods wherein the electrode is not used for applying the neuromodulation therapy (e.g. the purpose that is different from providing the movement cue).

Further, in some embodiments, the stimulation system provided by the present invention may also comprise means for operating the neuronal stimulation electrode according to its purpose. For instance, if the neuronal stimulation signal providing the movement cue is applied via an electric contact of a DBS electrode implanted for treatment of PD, the stimulation system provided by the present invention may also comprise the necessary means to generate, amplify and/or apply the neuromodulation therapy signal via the DBS electrode.

In this manner, system components such as a power supply, communication interfaces, memory, signal processing circuitry, etc. can be shared and be integrated into a single neurostimulation device providing both, the neuromodulation therapy signal and the neuronal stimulation signal that is adapted to provide the movement cue. This reduces, cost, complexity and power consumption of the combined stimulation system compared to using largely independent stimulation systems for each purpose alone.

Further, in some embodiments, the neuronal stimulation signal may comprise a signal or a pulse train signal designed to be perceived by the individual as periodic.

For instance, the neuronal stimulation signal may be designed such that it elicits periodically appearing sensory percept in the cortex of the individual. For example, the neuronal stimulation signal may elicit a periodically appearing pressure sensation of a body part such as a leg, a foot, a hand, a tongue etc. of the patient. Alternatively or additionally, auditory and/or visual sensory percepts may be elicited in a periodic manner.

For instance, such a signal designed to be perceived by the individual as periodic may comprise burst pulses, wherein each burst may comprise a series of signal spikes. In this case, the perceived periodicity of such a signal may then correspond to the repetition rate of the bursts pulses. For instance, a burst pulse may be 300 ms long and may comprise 42 signal spikes each having an amplitude of 1 mA.

In some embodiments, the periodicity of such sensory percepts may correspond to a characteristic of a movement related to the movement cue provided by the neuronal stimulation signal, such as a waking pace, a breathing rhythm, a dancing rhythm etc.

In this manner, the neuronal stimulation signal may be used to provide guidance to a patient desiring to perform a periodic or rhythmic movement or behavior such as walking, breathing and/or dancing.

Further, in some embodiments, the means for transmitting the neuronal stimulation signal may be further configured to control a frequency, a pulse width, a pulse shape and/or an amplitude of the neuronal stimulation signal transmitted to the electric contact of the neuronal stimulation electrode.

In this manner, a great variety of neuronal stimulation signals can be transmitted and be used to provide a great variety of different movement cues to the individual e.g. via elicited sensory percepts in the sensory cortex. Moreover, by controlling signal parameters such as the frequency, the pulse width, the pulse shape and/or the amplitude, the neuronal stimulation signal and thus also the provided movement cue can be tailored to the individual, e.g. via carrying out calibration and learning procedures specific to the individual.

For instance, the means for transmitting may be further configured to control a movement speed, a pace regularity and/or a balance of the individual via the frequency the pulse width, the pulse shape and/or the amplitude of the neuronal stimulation signal.

In this manner the provided system enables the design of closed-loop movement enhancement systems, wherein one or more characteristics of a movement of the individual are determined and then used to provide a feedback signal for the neuronal stimulation signal. In this way, the sensory quality of the provided movement cue can dynamically be adjusted to varying external conditions and/or changing movement characteristics.

Further, the means obtaining the neuronal stimulation signal may comprise means for selecting at least one neuronal stimulation signals to be transmitted to the neuronal stimulation electrode. For instance, the means for selecting may be adapted to select at least two different neuronal stimulation signals having different frequencies.

In this manner the individual, a therapy supervisor and/or an autonomous control logic may select different stimulation signals in response to different requirements. For instance, the individual may select a different signal frequency depending on whether he wants to carry out the movement at a slow or a fast pace. In addition, the intensity of the movement cue may be adjusted to be always clearly perceivable.

In some embodiments, a first neuronal stimulation signal may be adapted to control the movement speed, the pace regularity and/or the balance of the individual and a second neuronal stimulation signal is adapted to counteract a temporary movement impairment of the individual.

For instance, the second neuronal stimulation signal may be adapted to provide a FOG breakout signal to the individual and the first a gait pacemaker signal. In this manner the same stimulation system using the same neural interface (e.g. a DBS electrode) can be used to end a FOG period and to provide a gait pacemaker signal enhancing gait quality and reducing the occurrence frequency of FOG events.

Further, the means for transmitting the neuronal stimulation signal may be adapted to transmit at least two different neuronal stimulation signals to two different contacts of the neuronal stimulation electrode, preferably simultaneously.

In this way, auxiliary information can be provided to the individual together with the movement cue. For instance, while the movement cue is applied via the first electric contact, the second contact may be used to communicate a balance signal, information about the body posture, the position of the individual with respect to a reference position or a warning signal.

In another embodiment, the present invention provides a system for communicating proprioceptive information to an individual, comprising: means for obtaining information about the body posture of the individual, means for determining, based on the obtained information, a neuronal stimulation signal to be applied to at least one afferent axon targeting at least one sensory neuron in the cortex of the individual, wherein the determined neuronal stimulation signal corresponds to the proprioceptive information to be communicated and means for transmitting the determined neuronal stimulation signal to a neuronal stimulation means of the individual adapted to apply the determined neuronal stimulation signal to the at least one afferent axon.

Such a system can be used to provided proprioceptive information directly to the cortex of an individual either in order to substitute proprioceptive sensations that were impaired by a neurological disease or a lesion of the nervous systems of the individual or to provide artificial proprioceptive information which has no physiological counterpart. For instance, the determined neuronal stimulation signal may be configured to elicit a conscious or subconscious sensory percept in the cortex of the individual.

In contrast to the prior art the present invention enables supplementation of natural afferent proprioception by artificial means to aid the individual in the integration of movement, posture and proprioception.

For example, the information about the body posture may comprise at least one of:
  a. information about an articulation state of a joint of the individual;
  b. information about a flexing angle of a joint of the individual;
  c. information about the balance of the body of the individual;
  d. information about a tone of a muscle of the body of the individual;
  e. information about a position of a part of the body of the individual with respect to a reference position.
  f. information about a surface contact of a part of the body of the individual.

Further, the means for obtaining the information about the body posture of the individual may comprise at least one of:
  a. a pressure sensor;
  b. a tension sensor;
  c. a balance sensor;
  d. an acceleration sensor;
  e. a temperature sensor;
  f. an image sensor;
  g. a force sensor;
  h. a distance sensor;
  i. an angle sensor;
  j. a speed sensor;

By using one or more of such sensors an accurate model of the body posture of the individual may be determined and be used to determine a tailored neuronal stimulation signal that is adapted to communicate precise and reliable proprioceptive information directly to the cortex of the individual.

Further, the means for determining the neuronal stimulation signal may comprise means for accessing a data storing means storing relations, specific for the individual, between a plurality of proprioceptive information and a plurality of corresponding neuronal stimulation signals.

This embodiment greatly improves the efficiency and flexibility of communicating the desired proprioceptive information to the cortex of the individual. For instance, a communication device that interfaces with or uses the provided system can easily determine and directly transmit the specific neuronal stimulation signal corresponding to a desired proprioceptive information via stimulation of afferent axons targeting sensory neurons in the cortex of the individual.

For instance, in some embodiment of the present invention, the stored relations between the proprioceptive information and the corresponding neuronal stimulation signals may be based at least in part on one or more of: spatial information for the at least one afferent axon, spatial information for the at least one neuronal stimulation means, neuronal connectivity information for the at least one afferent axon, an electric field distribution associated with the neuronal stimulation means, functional neuroimaging data for the individual, diffusion tensor imaging data for the individual, neuroanatomical reference data being relevant for the individual, cortical excitation data for the individual, sensory perception data for the individual, behavioral data based at least in part on subjective experiences of the individual and/or an optimization procedure for maximizing the number of proprioceptive information that can be perceived by the individual.

Further, the stored specific relations may be based at least in part on proprioceptive learning data for the individual, the learning data associating the plurality of proprioceptive information with the plurality of corresponding neuronal stimulation signals.

Further, the means for determining the neuronal stimulation signal may comprise means for determining an excitation probability of the at least one afferent axon and/or the at least one sensory neuron based at least in part on the obtained spatial information, preferably by using a finite element method and/or a neuronal compartment model.

In this manner active electric properties (e.g. the non-linear neuronal excitability) of the at least one axon can be taken into account by the system when determining the neuronal stimulation signal, thereby further enhancing the specificity and accuracy of the proprioceptive information to be communicated.

In another embodiment, the present invention provides a system for communicating movement information to an individual, comprising means for providing a first neuronal stimulation signal to the cortex of an individual adapted to provide a movement cue for the individual and means for providing a second neuronal stimulation signal to the cortex of the individual adapted to provide proprioceptive information to the individual, wherein the first and the second neuronal stimulation signal are provided together to the cortex of the individual.

In many cases, neurological movement impairments also entail a degradation of physiological proprioceptive information reaching the cortex of the affected individual via the sensory nervous system. Thus, by communicating proprioceptive information together with a movement cue via a neuronal communication interface the system provided by the present invention can substantially enhance the success of movement impairment therapies.

Similar as for other embodiments discussed above, the first and/or the second neuronal stimulation signal may be applied via at least one portion of a neural stimulation electrode already implanted for a purpose different from communicating the movement information (e.g. for the purpose of applying a neuromodulation therapy to the thalamus or the sub-thalamic nucleus).

Alternatively, the first and/or the second neuronal stimulation signal may also be applied via different neural interface means such as transcranial stimulation means, sub-dural electrode arrays, spinal cord stimulation means, optogenic neuronal interface means and/or peripheral nerve stimulation means.

Further, the proprioceptive information conveyed by the second stimulation signal may be related to a body part of the individual that is involved in a movement of the individual associated with the movement information to be communicated. For instance, the second neuronal stimulation signal comprises one of the following information:
  a. information about an articulation state of a joint of the individual;
  b. information about a flexing angle of a joint of the individual;
  c. information about the balance of the body of the individual;
  d. information about a tone of a muscle of the body of the individual;
  e. information about a position of a part of the body of the individual with respect to a reference position
  f. information about a surface contact of a part of the body of the individual.

In this manner, the individual can be provided with relevant proprioceptive information that can assist in performing a movement task such as walking, dancing, etc.

Similar to other embodiments discussed above, the first neuronal stimulation signal may comprise a signal (e.g. a pulse train signal) that is designed to be perceived as periodic by the individual.

Further, the means for providing the first and/or the second neuronal stimulation signal may be adapted to control a frequency, a pulse width, a pulse shape and/or an amplitude of the first and/or the second neuronal stimulation signal and/or adapted to control a relative timing between the first and the second neuronal stimulation signal.

In this manner, the provided system can ensure that both neuronal stimulation signals can be applied to the cortex of the individual in a manner that is specific to the individual.

In particular, the second neuronal stimulation signal may be provided at a rate that is more than 2 times, preferably more than 5 times, more preferably more than 10 times and even more preferably more than 20 times larger than a frequency of the first neuronal stimulation signal.

Providing the second neuronal stimulation signal more often than the first one allows the individual to use the provided proprioceptive information while performing the movement associated with the movement cue provided by the by the first neuronal stimulation signal.

Further, the second neuronal stimulation signal may be provided quasi-continuously with respect to the first neuronal stimulation signal, e.g. at a rate that is much larger than a frequency of the first neuronal stimulation signal.

Similar as for other embodiments discussed above, the provided system may further comprise means for obtaining information about the body posture of the individual via at least one of:
  a. a pressure sensor;
  b. a tension sensor;
  c. a balance sensor;
  d. an acceleration sensor;
  e. a temperature sensor;
  f. an image sensor;
  g. a force sensor;
  h. a distance sensor;
  i. an angle sensor;
  j. a speed sensor.

Using one or more of such sensors allows the system to obtain precise information on the body posture of the individual. In several embodiments, the means for obtaining information about the body posture of the individual may be integrated into at least one of the following:
  a. a piece of apparel,
  b. a piece of footwear,
  c. a prothesis,
  d. an orthosis,
  e. an exoskeleton,
  f. an autonomous robotic companion,
  g. a wearable electronic device.
  h. an implanted device.

Further, the various systems provided by the present invention may also comprise means for receiving a neuronal measurement signal corresponding to a neuronal excitation pattern recorded via a neuronal excitation measurement device.

Further, the neuronal measurement signal may be received from at least one of the following:
  a. an electroencephalography, EEG, device;
  b. a neuro-electrode,
  c. a deep brain stimulation electrode,
  d. a sub-dural electrode;
  e. a sub-dural electrode array;
  f. a connected wearable device;
  g. a transcranial excitation measurement device.

By integrating measurements of neuronal excitation patterns the systems provided by the present invention can be used for closed-loop and/or neurofeedback applications. For instance, the system may be configured to receive a signal corresponding to a neuronal excitation pattern associated with a movement intention and/or to motor-sensory information of the individual.

In this manner, the system could be directly controlled by the mind of the individual. For instance, instead of adjusting the walking pace via a control device such as a smartphone the individual could control the pace by merely thinking of walking slowly or fast. The system would then record the corresponding neuronal excitation pattern and derive the required stimulation signal parameters (e.g. frequency, pulse width amplitude etc.) that correspond to the walking pace intended by the individual. With training the individual can even regain full dynamic control over his walking pace or other movements supported by the systems provided by the present invention.

In another embodiment, the present invention provides an electronic information processing device, comprising a system according to any of the embodiments discussed above. For instance, the functionalities of any of the above systems may be implemented on a general-purpose signal processing device such as a smartphone comprising memory, digital and analog signal processing circuitry as well as interface means (e.g. a wireless communication interface) that allows to transmit neuronal stimulation signals to various kinds of neural interface means such as a DBS device.

In another embodiment, the present invention provides a distributed electronic information processing system, comprising the system according to any of the embodiments discussed above. For instance, some system components may not be collocated in a single device but may be communicatively connected via a wired or wireless communication interface.

In another embodiment, the present invention provides a computer program, comprising instructions to implement the functionalities of a system according to any of the embodiments discussed above, when being executed by an electronic information processing device or a distributed electronic information processing system.

4. SHORT DESCRIPTION OF THE FIGURES

Figure 2:
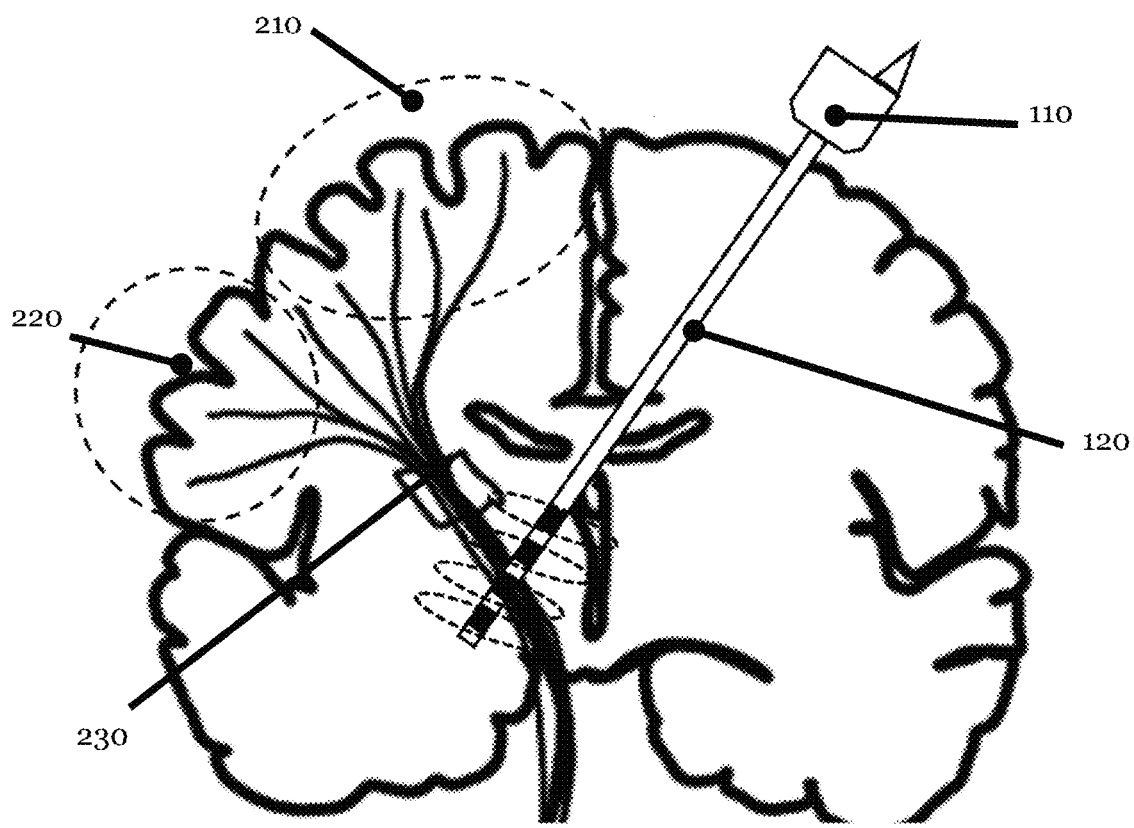
Figure 3:
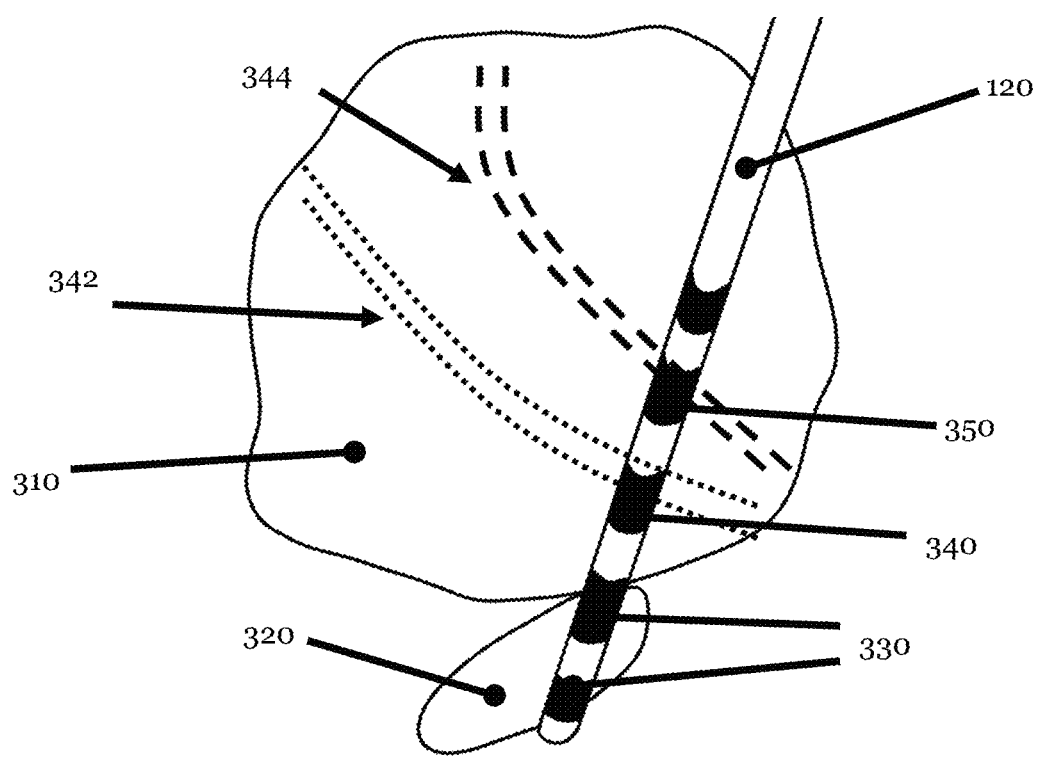
Figure 4A:
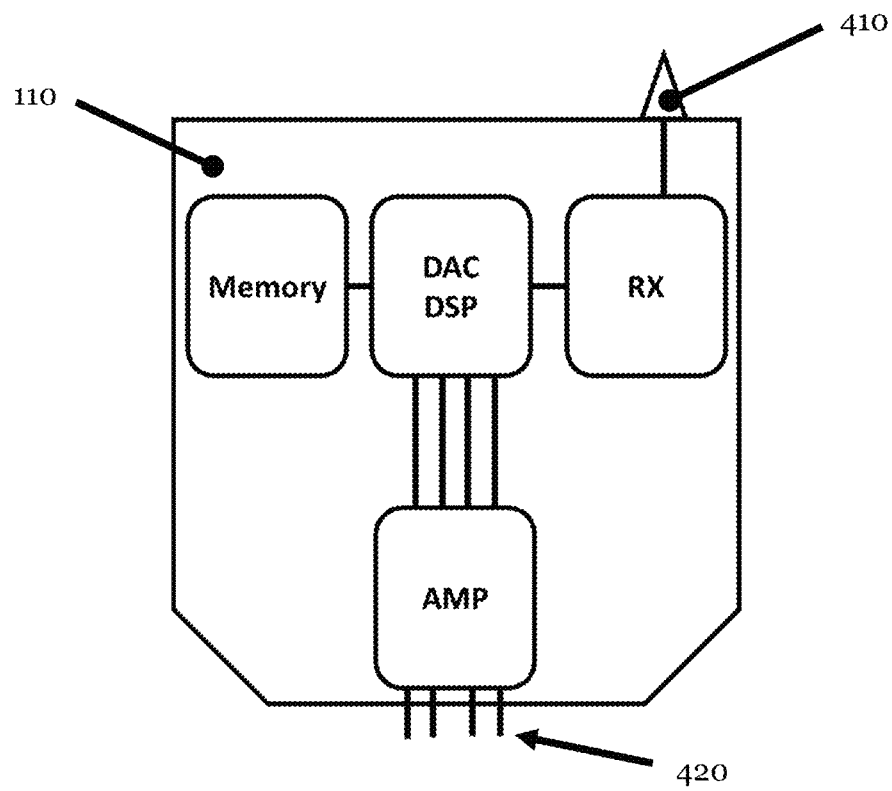
Figure 4B:
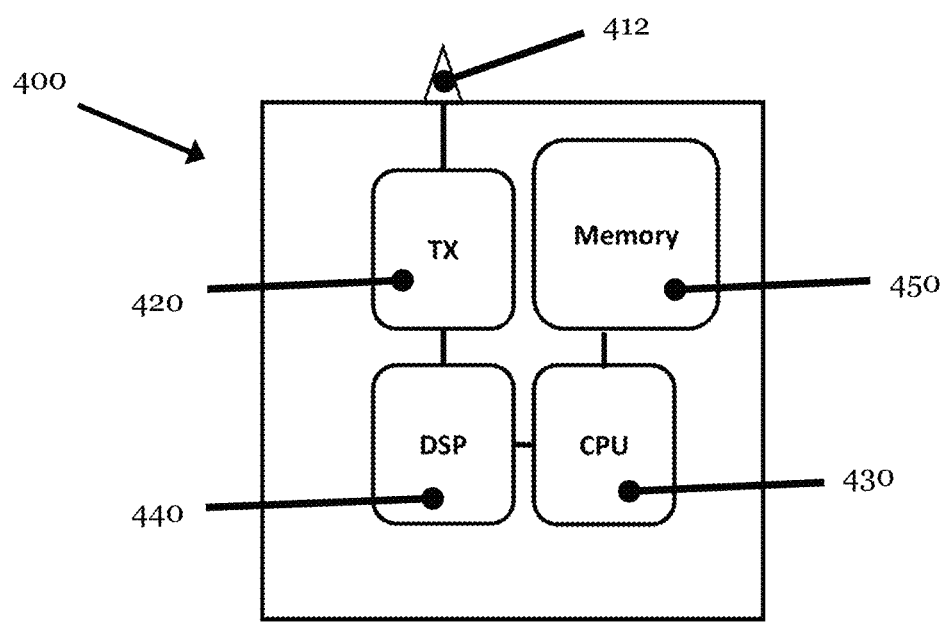
Figure 5:
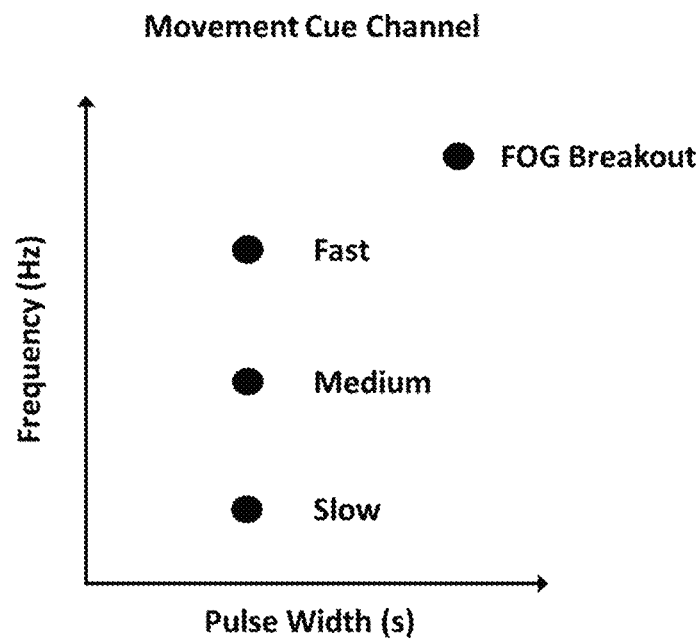
Figure 6:
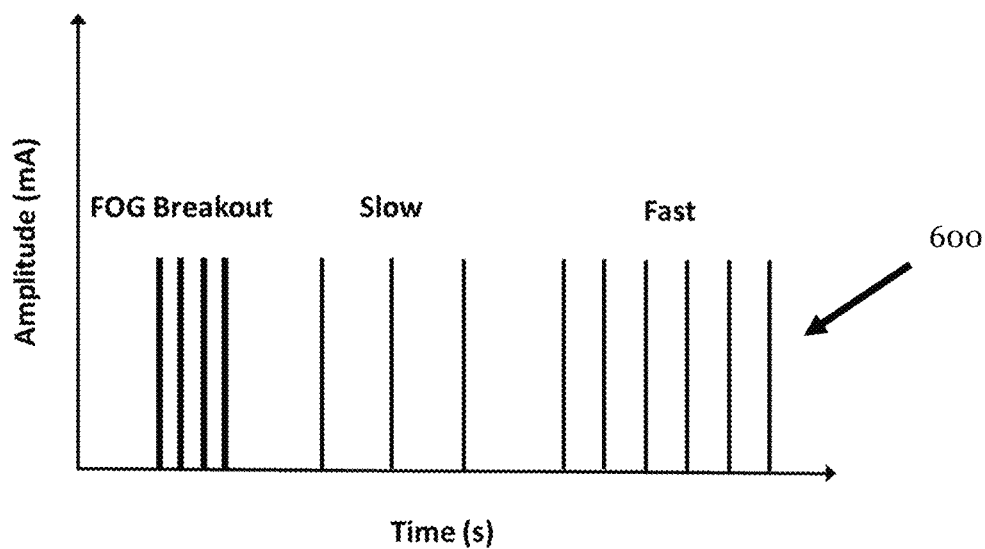
Figure 7:
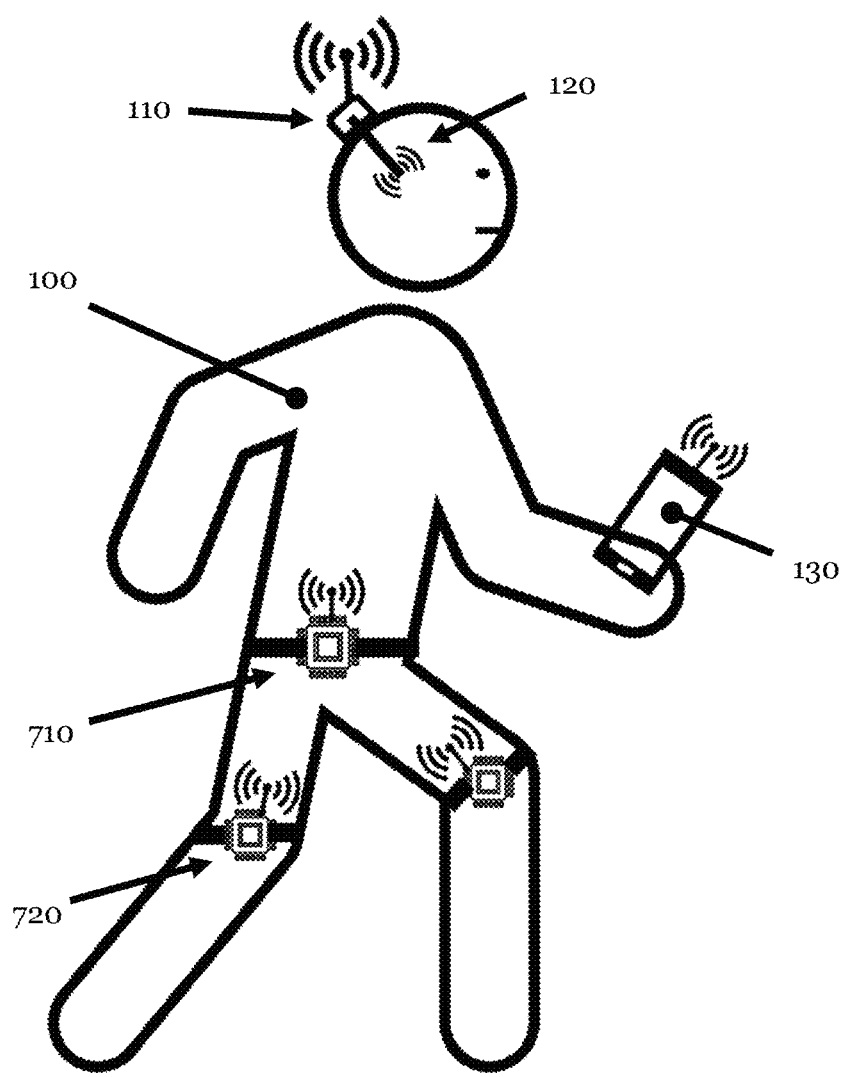
Figure 8:
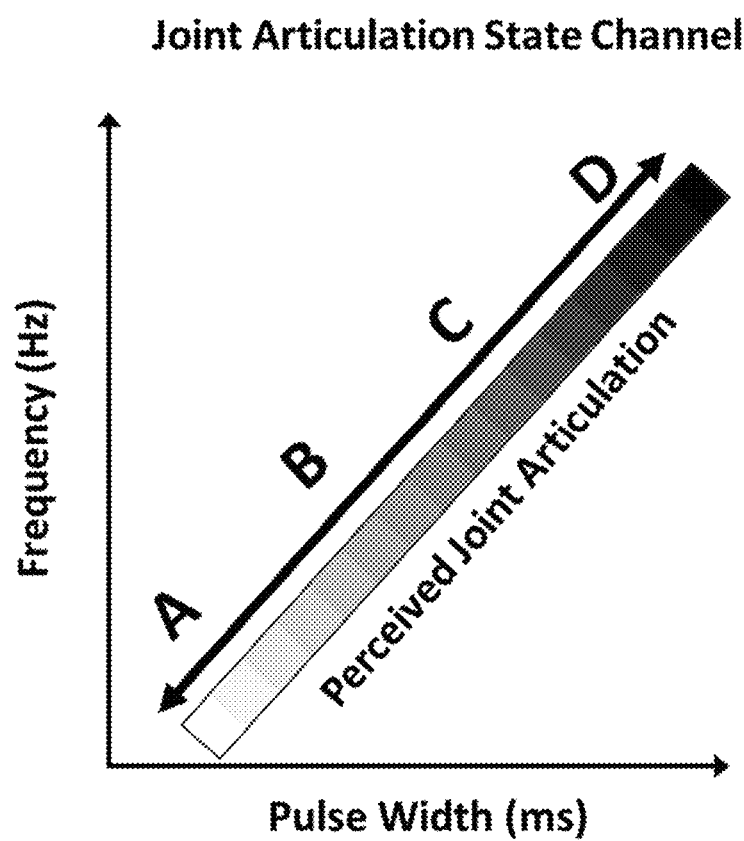
Figure 9:
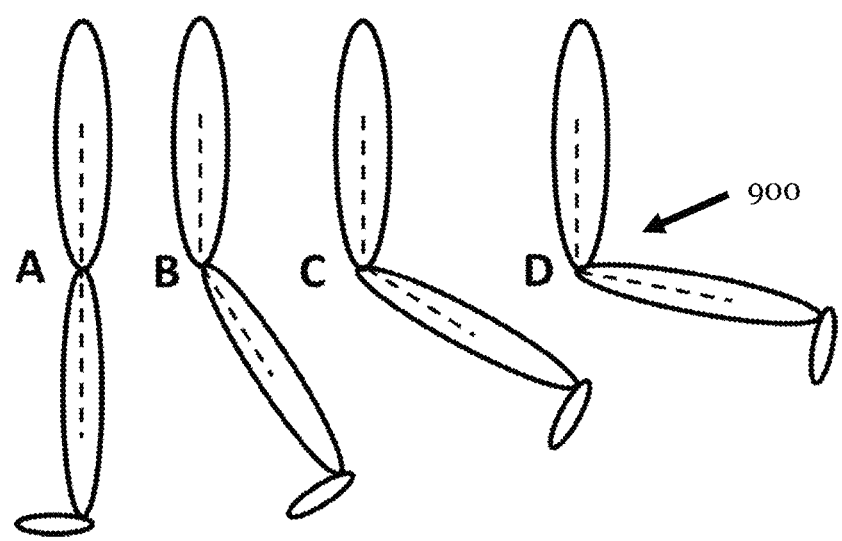
Figure 10:
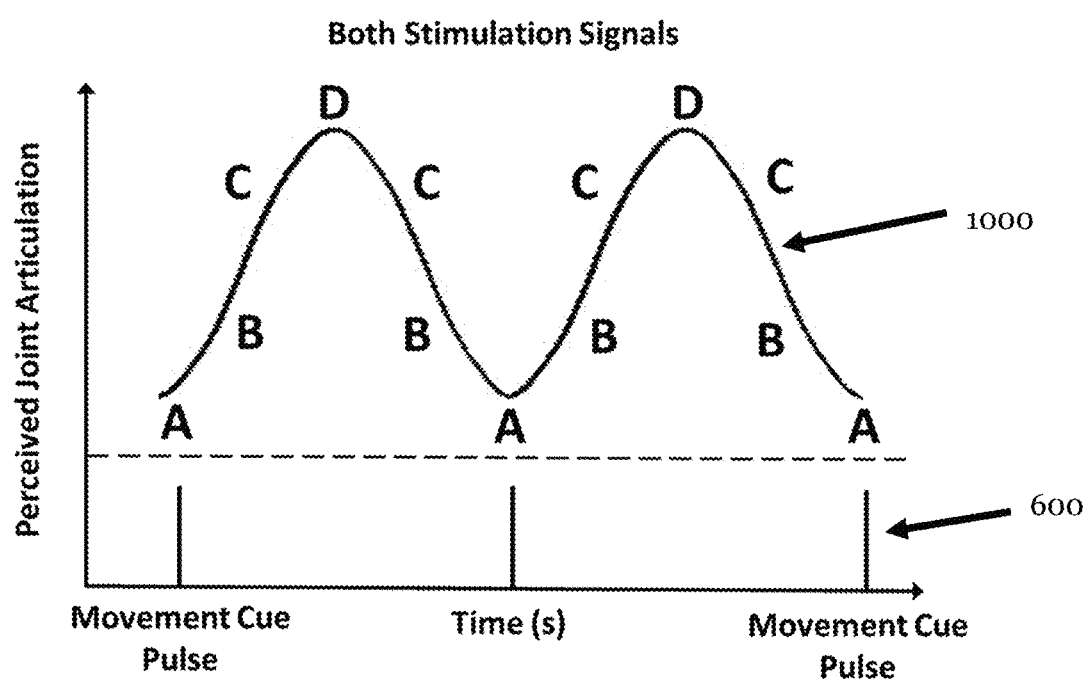

Aspects of the present invention are described in more detail in the following by reference to the accompanying figures. These figures show:

FIG. 1 a diagram illustrating an individual operating a neuronal stimulation system according to an embodiment of the present invention;

FIG. 2 a diagram illustrating a neuronal stimulation electrode for stimulating afferent axons targeting the sensory cortex of an individual. The neuronal stimulation electrode can be interfaced with a neuronal stimulation system according to an embodiment of the present invention;

FIG. 3 a diagram illustrating a therapeutic multi-contact neuromodulation electrode adapted for modulation of brain nuclei associated with a movement impairment. Unused contacts of the electrode can be used for stimulating afferent axons targeting the sensory cortex of an individual via a neuronal stimulation system according to an embodiment of the present invention;

FIG. 4A a block diagram of a neuronal stimulation signal generator for driving a neuronal stimulation electrode which can be interfaced with a neuronal stimulation system according to an embodiment of the present invention;

FIG. 4B a block diagram of a neuronal stimulation system according to an embodiment of the present invention;

FIG. 5 a diagram illustrating how a movement cueing channel can be implemented using a neuronal stimulation system according to an embodiment of the present invention;

FIG. 6 a diagram illustrating exemplary neuronal stimulation signals adapted to provide a movement cue and a FOG break-out signal;

FIG. 7 a diagram illustrating an individual operating a neuronal stimulation system according to a further embodiment of the present invention;

FIG. 8 a diagram illustrating how a proprioceptive information channel can be implemented using a neuronal stimulation system according to an embodiment of the present invention;

FIG. 9 a diagram illustrating how the proprioceptive information channel of FIG. 8 can be used to communicate information on the articulation state of a knee joint of an individual;

FIG. 10 a diagram illustrating the relative timing of the movement cue channel of FIG. 6 and the joint articulation state channel of FIGS. 8 and 9 while the individual depicted in FIG. 7 performs a walking task.

5. DETAILED DESCRIPTION OF SOME EXEMPLARY EMBODIMENTS

In the following, some exemplary embodiments of the present invention are described in more detail, with reference to neuronal stimulation and/or communication systems that can be interfaced with neuronal stimulation electrodes such as deep brain stimulation (DBS) electrodes. However, the systems provided by the present invention can also be used with different neuronal stimulation means (e.g. optoneuronal) that are capable to stimulate the sensory cortex of an individual e.g. via stimulating afferent axons targeting the sensory cortex. While specific feature combinations are described in the following with respect to the exemplary embodiments of the present invention, it is to be understood that the disclosure is not limited to such embodiments. In other words, not all features have to be present for realizing the invention, and the embodiments may be modified by combining certain features of one embodiment with one or more features of another embodiment. Specifically, the skilled person will understand that features, components and/or functional elements of one embodiment can be combined with technically compatible features, components and/or functional elements of any other embodiment of the present invention.

FIG. 1 depicts an individual too, e.g. a PD patient, that has been implanted with a neuronal stimulation electrode 120 such as a DBS electrode that may have multiple independently controllable electric contacts, as illustrated in FIG. 3 below. For instance, the neuronal stimulation electrode 120 may be already implanted into the brain of the individual too for the purpose of providing a neuromodulation therapy for certain PD symptoms such as tremor, dystonia and/or rigidity. However, the neuronal stimulation electrode 120 may also be implanted for other purposes such as for the purpose of neuronal communication and/or treatment of other movement impairments and neurological diseases such as epilepsy. Alternatively, the electrode 120 may also be implanted dedicated as an interface for the systems provided by the present invention.

The individual 100 may be further equipped with a neuronal stimulation signal generator device 110 that may be arranged on the head of the individual 100 or somewhere else on or in the vicinity of the body of the individual 100. The neuronal signal generator 110 may be in wireless communication (e.g. via a Bluetooth or similar wireless interface) with a control device 130, that may be implemented by a smartphone or a similar electronic information processing device. Depending on implementation details the systems provided by the present invention may be implemented by the control device 130, the neuronal signal generator 110, an additional system (such as the system 400 of FIG. 4B) or a combination thereof. For instance, the control device 130, the signal neuronal signal generator device 110 or both may be provided with application specific hardware and/or software modules comprising circuitry and/or software instructions to implement a system according to the present invention.

The control device 130 may provide the individual with a user interface to adjust the neuronal stimulation signals and/or the neuromodulation therapy applied via the signal generator 110 and the neuronal stimulation electrode 120. For instance, the individual 100 may adjust signal parameters such as a signal frequency, a pulse width, a pulse shape and/or a signal amplitude. For example, the individual may use the control device 130 to select a perceived periodicity of a movement cue provided by a neuronal stimulation signal to the cortex of the individual 100. For example, if the movement cue is used to provide guidance to the individual 100 during a movement such as walking, the control device 130 may be used to select and set a movement pace associated with the perceived periodicity of the movement cue.

FIG. 2 depicts a diagram illustrating a neuronal stimulation electrode 120 for stimulating afferent axons 230 targeting sensory neurons in the cortex of a human brain. The afferent axons 230 may target different areas 210, 220 of the cortex that may be related to different sensory modalities (e.g. touch, temperature sense, vision, hearing, etc.) and/or different body regions (e.g. cochlea, retina, hand, tongue, foot etc.) from which the respective sensory modality is perceived by the respective area of the cortex. For instance, the cortical area 210 may be a somatosensory area of the right foot and the cortical area 220 may be a somatosensory area of the left hand.

The afferent axons 230 are connected via synapses (not shown) with their respective target neurons in the respective sensory area 210, 220. For instance, the axons 230 may be thalamocortical axons relaying sensory information from the thalamus to the cerebral cortex. The neuronal stimulation electrode 120 may comprises a plurality of independently controllable electric contacts (see FIG. 3 below) that may be arranged in the vicinity of a bundle of afferent axons 230 targeting the sensory areas 220 and 210 of the cerebral cortex.

In the illustrated example, the neuronal stimulation electrode 120 is connected to a neuronal stimulation signal generator 110, which is adapted to apply neuronal stimulation signals to the afferent axons 230, e.g. via independently controllable electric contacts of the neuronal stimulation electrode 120. In addition, the neuronal stimulation electrode 120 may further comprise a wireless interface for interfacing the signal generator 110 with a neuronal stimulation system which may be adapted to obtain and/or determine the waveform and/or signal parameters (e.g. pulse width, pulse shape, frequency, amplitude, number of pulses etc.) of the neuronal stimulation signal that is generated and applied by the signal generator 110 to the afferent axons 230 via the stimulation electrode 120.

For instance, the neuronal stimulation system provided by the present invention may determine the waveform and/or signal parameters of the neuronal stimulation signal such that a desired sensory percept is elicited in a desired area of the sensory cortex of the individual. In some embodiments of the present invention, the cortex of the individual which is receiving the neuronal stimulation signal (i.e. via afferent action potentials of the stimulated afferent axons 230) may associate the corresponding sensory percept with a movement cue and/or other type of movement related information such as proprioceptive information relating to the body posture of the individual operating the neuronal stimulation system. For example, similar to learning how to understand Morse code, the individual may have previously participated in a learning procedure establishing an associative link between a given sensory percept elicited by a given stimulation signal and a corresponding movement cue (see FIGS. 5 and 6 below) or a piece of proprioceptive information (e.g. see FIGS. 8 and 9 below) that is to be communicated to the individual via the neuronal stimulation electrode 120.

In this approach no nuclei or neuron-rich grey matter are preferably targeted by the neuronal stimulation electrode 120 but preferably the axon-rich white matter of the brain, which contains the information transmitting pathways the brain uses for natural neural communication. In this manner, the present invention provides a white-matter computer-brain-interface (CBI), i.e. a system that generates and provides electrical signals the brain can interpret as meaningful input, e.g. as a rhythmic movement cue or any other type of movement related information such as a commence movement trigger (e.g. a FOG break-out signal) or information about the current body posture of the individual (e.g. proprioceptive information). As discussed in section 3 above, such information may be provided by different types of measurement devices or sensors (see also FIG. 7).

In other embodiments of the present invention, the neuronal stimulation electrode 120, the signal generator 110 and/or the wireless interface may also be part of an integrated neuronal stimulation and/or communication system, e.g. if said components are customized for the intended application. For instance, a neuronal communication system may comprise of specialized communication software running on a multi-purpose information processing device such as a smartphone and a customized assembly of signal generator 110 and stimulation electrode 120 which communicate with the multi-purpose communication device via a wireless interface using conventional wireless data transmission technology such as Wi-Fi, Bluetooth and/or NFC.

In other embodiments of the present invention the neuronal stimulation electrode 120 may be directly connected via wires to a neuronal stimulation system comprising a data processing system and a signal generator similar to the signal generator no. In this case a wireless interface is not needed.

FIG. 3 depicts of a multi-contact neuromodulation electrode 120 adapted for neuromodulation of the sub-thalamic nucleus 320 via electric contacts 330. The electrode 120 can also be used for stimulating afferent axons 342, 344 projecting from the thalamus 310 to the sensory cortex of an individual via a neuronal stimulation system according to the present invention. For example, neuronal stimulation signals may be provided by unused contacts 340, 350 of the neuromodulation electrode 120 that was implanted for a therapeutic purpose (e.g. neuromodulation of the subthalamic nucleus 320 via the therapeutic electric contacts 330) different from providing the neuronal stimulation signal to the afferent sensory axons 344, 342. For instance, the contacts that are not used for neuromodulation of the sub-thalamic nucleus 320 may be used to provide a sensory movement cue and/or proprioceptive information to the cortex of the individual. An example of such a sensory movement cue may be a rhythmic sensory percept elicited by a neuronal stimulation signal applied to the axons 344 targeting a cortex area related to a touch sensation for instance in the left foot.

In many cases, a DBS electrode 120 that is used as a neuromodulator, e.g. for treatment of PD symptoms, is not always active and/or may comprise independently controllable contacts that are not required for achieving the therapeutic purpose. Thus, the neuromodulation electrode can also be used for applying neuronal stimulation signals provided by a system according to the present invention. For DBS electrodes, specifically, some of the electrode contacts located outside of the stimulation area of interest are not used. However, if implantation in e.g. the subthalamic nucleus 320 is conducted for the tip contacts 330 to control, for example, the primary PD symptoms more distal contacts 340, 350 could be used in combination with the above disclosed invention to communicate a movement cue and/or a continuous movement biofeedback signal into the brain the patient can utilize to navigate better and/or break free from FOG.

FIG. 4A depicts is a block diagram of a neuronal stimulation signal generator 110 which can be used to apply neuronal stimulation signals to afferent axons 230 via a neuronal stimulation electrode such as the stimulation electrode 110 of FIGS. 1-3. The neuronal stimulation signal generator 110 may comprise a wireless interface 410 for communicating with a remote neuronal stimulation system (e.g. see FIG. 4B) which may be adapted to obtain, to determine, to select and/or to transmit a waveform and/or signal parameter of the neuronal stimulation signal to the signal generator 110 in order generate a neuronal stimulation signal adapted to elicit a desired sensory percept associated with a movement cue (see FIGS. 5 and 6) and/or proprioceptive information (see FIGS. 8 and 9).

For instance, the neuronal stimulation signal generator 110 may receive digital data packets specifying a desired neuronal stimulation signal via the wireless interface 410. Receiver (RX) circuitry may process (e.g. filter, amplify, mix, down-convert to baseband etc.) the received digital data packets and feed the processed digital data packets to a digital signal processor (DSP) with may comprise an integrated digital-to-analog converter (DAC). The DSP then processes the digital data packets to generate one or more neuronal stimulation signals which may then be amplified and applied to a neuronal stimulation electrode such as electrode 120 of FIG. 2 and FIG. 3 by an output amplifier (AMP). For instance, the output AMP may be configured to drive four (or any other number) independently controllable electric contacts 330, 340, 350 of a stimulation electrode such as electrode 120 via the output wires 420.

In other embodiments, the DSP may receive the digital data packets specifying the neuronal stimulation signal also via a wire-based interface or directly from a collocated processing circuit (e.g. a CPU) which may be adapted to determine the waveform and/or signal parameters of a desired neuronal stimulation signal corresponding to a desired sensory movement cue and/or proprioceptive information to be elicited in the cortex of the to the individual.

FIG. 4B depicts a block-type circuit diagram of an exemplary neuronal stimulation system 400 according to an embodiment of the present invention. The neuronal stimulation system 400 may for instance comprise a wireless interface 412 and transmitter (TX) circuitry for communicating (e.g. via Bluetooth or a similar interface) with a neuronal stimulation signal generator such as the generator circuit 110 described above with reference to FIG. 4A. The TX circuitry may be adapted to process (i.e. filter, modulate, mix, amplify, and/or upconvert) digital data packets to be communicated via the wireless interface 412. The neuronal stimulation system 400 may further comprise a digital signal processor (DSP) operably connected with the TX circuitry and adapted to provide digital data packets specifying the waveform and/or the signal parameters (e.g. frequency, phase, pulse width, pulse amplitude, pulse shape, channel count, etc.) of a desired neuronal stimulation signal to be applied via a neuronal stimulation electrode such as the electrode 120 of FIGS. 2 and 3 and via a neuronal stimulation signal generator such as signal generator 110 of FIG. 4A.

The neuronal stimulation system 400 may further comprise general data processing circuitry such as a CPU operably connected to the DSP and at least one digital memory device operably connected to the CPU. The CPU 320 and the memory may interact to determine a desired neuronal stimulation signal corresponding to a desired sensory percept such as the desired movement cue and/or the desired proprioceptive information to be communicated to the cortex of the individual.

For instance, the memory may contain a personalized communication library for the individual, the library storing relations between a plurality of movement cues and/or perceptive information blocks and a plurality of corresponding neuronal stimulation signals.

Such a stimulation library can be calibrated for each individual through neuroimaging and/or individualized testing of the individual. Neuroimaging may first be used to identify theoretically possible ranges of activation for an individual stimulation electrode while individualized testing determines which points in the parameter space of stimulation signal parameters (for details see FIG. 5 and FIG. 8 below) can be perceived and decoded by the cortex of the individual. It should be emphasized that conscious individualized testing of an individual is merely one specific example how to generate the individualized relations stored in the memory. In other embodiments such relations may also be obtained from unconscious patients, e.g. through the non-invasive observation of corresponding functional MRI responses on the somatosensory cortex or EEG recordings.

Further, once or while the communication library (i.e. the plurality of relations stored in the memory) is established or is being established for an individual a specific training procedure can be executed (again not necessarily in a conscious individual). As long as the cortex of the individual responds to classical conditioning, pair learning can be executed. In the context of the present invention, such a pair consists of a given sensory percept corresponding to a given neuronal stimulation signal and a movement cue and/or a piece of proprioceptive information to be associated with said given sensory percept and the corresponding neuronal stimulation signal.

Importantly, the type of information to be conveyed via the neuronal stimulation system 400 whether it is a movement cue, a FOG breakout signal or a piece of proprioceptive information can be chosen freely. Any information or message which can be broken down into message blocks (i.e. pieces of conceptual information that can be decoded by the cortex of an individual) can be transmitted. This includes continuous signals such as signals needed for e.g. an artificial balance, orientation signals or other sensor measurement signals.

Learning paradigms for continuous signals deviate from classical conditioning, since they involve more interactive training scenarios where utilization of the signal is a relevant success factor (e.g. orientation in an artificial virtual environment using the input signal). Continuous signals (e.g. intensity) also deviate from signal configurations for messages containing sequentially delivered message blocks. In the case of continuous signals, intensity might be coded via either pulse width or frequency variations (or combinations of the two; see FIG. 8 below), while not varying the location and target areas in the sensory cortex targeted by the recruited axon fibers.

FIGS. 5 and 6 illustrates how embodiments of the present invention can be used to establish a sensory movement cueing channel to the to the cortex of an individual and to use said cueing channel to provide a periodic movement cue and a FOG break-out signal that may be used for behavior modification, e.g. to support the individual during a walking task.

For instance, three different walking paces (e.g. 1 step per second, 0.5 steps per second, 2 steps per second) may be encoded by providing a pulse train signal via a neuronal stimulation interface and system as discussed above. Such a pulse train (being characterized by signal parameters such as pulse width, pulse frequency, pulse shape and/or pulse amplitude) may elicit a periodic/rhythmic sensory percept in the targeted area of the sensory cortex of the individual. For instance, such a pulse train signal may be configured to elicit a periodically appearing tough sensation in the palm of the right hand or in a leg of the individual. Similar to an auditory movement cue provided to the individual via earphones such a neuronal movement cue may help the individual to walk at a constant pace and without experiencing a FOG period. Moreover, the same neuronal communication channel can also be used to communicate a FOG breakout signal to the individual. For instance, the FOG breakout signal may be encoded by choosing a different combination of pulse train parameters such as a combination of a larger pulse frequency and a larger pulse width as indicted in FIG. 5.

FIG. 6 illustrates a typical use scenario of a neuronal stimulation system provided by the present invention. When occurrence of a FOG event has been determined (either by the neuronal stimulation system itself, a human supervisor or a control device associated with the individual performing the walking task) the neuronal stimulation system may obtain the FOG breakout signal (e.g. from its memory or via a wireless communication interface) and transmits it to an electric contact of a neuronal stimulation electrode such as the DBS electrode illustrated in FIGS. 2 and 3 to suppress the FOG event.

After a FOG event has been suppressed the neuronal stimulation system can switch into a pacemaker operation mode and may apply a slow periodic movement cue to help the individual to resume normal walking. After the individual has resumed slow walking he could provide a user input to the neuronal stimulation system indicating the intention to switch from the slow movement cue to a faster one.

Such user input may for example be provided via a control device such as a smartphone or via a neuronal excitation measurement equipment recording a neuronal excitation pattern corresponding to a motor intent of the individual. For instance, such a neuronal excitation measurement equipment may involve recoding from the contacts of the same neuronal electrode that is also used for applying the neuronal stimulation signal (e.g. in the form of Local Field Potentials). In some embodiments the system may also comprise an EEG device, a sub-dural electrode array and/or a transcranial excitation measurement device.

Such neuronal excitation measurement equipment may be used to provide the individual with an essentially closed loop stimulation system, wherein measurements motor related neuronal excitation patterns directly affect how the neuronal stimulation system is operating.

FIG. 7 depicts an individual 100, e.g. a PD patient, having been implanted with a neuronal stimulation electrode 120 such as a DBS electrode that may have multiple independently controllable electric contacts, as illustrated in FIG. 3. In addition to the devices discussed above with reference to FIG. 1 the individual 100 may further be equipped with sensors 710 and 720 that are configured to obtain information on the body posture of the individual 100. For instance, sensor 710 may be configured to measure the balance of the body of the individual 100 while the sensors 720 may be configured to measure the articulation state/flexing angle of the knee joints of the individual 100.

The sensors 710, 720 may be in wireless communication with the neuronal signal generator 110, the control device 130 and/or a neuronal stimulation system similar to the one discussed above with reference to FIG. 4B.

The measurement signals (providing information about the body posture of the individual 100) may be transmitted by the sensors 710 and 720 to the processing means of a neuronal stimulation system. The system may then determine, based on the obtained information, a neuronal stimulation signal to be applied to at least one afferent axon targeting at least one sensory neuron in the cortex of the individual, wherein the determined neuronal stimulation signal corresponds to proprioceptive information that is communicated to the individual.

For instance, as illustrated in FIG. 8 and FIG. 9 neuronal stimulation system may use the measurements of the knee joint sensors 720 to determine a neuronal stimulation signal that is adapted to communicate the articulation state of the knee joint to the cortex of the individual. As shown in FIG. 8, the articulation state of the knee joint may be encoded by a combination of signal parameters such as pulse width and pulse frequency of a pulse train signal. In the example shown in FIG. 8 a low frequency pulse train having a short pulse width (A) corresponds to a knee joint that is essentially fully stretched out (A) whereas a high frequency pulse train having a long pulse width (D) corresponds to a knee joint that is almost fully bent (D).

FIG. 10 illustrates how the movement cueing channel of FIGS. 5 and 6 and the proprioceptive information channel of FIGS. 8 and 9 can be combined to improve the performance of a neuronal stimulation system intended for treatment of movement impairments. In the illustrated example a neuronal stimulation signal that is providing the joint articulation state information (e.g. the proprioceptive information channel) is applied quasi-continuously while the individual performs a movement (e.g. walking, dancing etc.) paced by the movement cue signal. If the individual walks synchronized with the movement cue signal every time a movement cue pulse is perceived by the individual the joint articulation signal communicates a fully stretched state (A) of the knee joint to the individual. Between two movement cue pulses the knee joint of the individual first bends (A-B-C-D) and then stretches out again (D-C-B-A).

Compared to systems that only provide movement cues a system providing both, a m movement cue and proprioceptive information together to the cortex of an individual substantially improves the movement performance of the individual because synchronizing the movement of the individual with an external movement cue is much easier if proprioceptive information is provided as feedback to the brain that indicates the phase of the movement relative to the timing of the movement cue.

The invention claimed is:
1. A system for stimulating a sensory cortex of an individual, comprising:

a. transmitter circuitry;

b. a processor coupled to a non-transitory memory and the transmitter circuitry, wherein the non-transitory memory stores one or more neuronal stimulation signals, wherein the processor is configured to execute program instructions stored on the non-transitory memory to cause the transmitter circuitry to:

transmit a first neuronal stimulation signal of the one or more neuronal stimulation signals to a neurostimulation device of the individual configured to stimulate afferent sensory axons of a central nervous system of the individual projecting to the sensory cortex of the individual, wherein the neurostimulation device is further configured to apply a neuromodulation therapy to the central nervous system of the individual, wherein the first neuronal stimulation signal is applied via one or more electric contacts of a neurostimulation electrode of the neurostimulation device that are not used for applying the neuromodulation therapy, and wherein the first neuronal stimulation signal is configured to provide a periodic movement cue to the sensory cortex of the individual; and transmit a neuromodulation therapy stimulation signal to the neurostimulation device to apply the neuromodulation therapy via one or more electric contacts of the neurostimulation electrode that are not used for applying the first neuronal stimulation signal; and c. a user interface configured to receive user input for selecting the first neurostimulation signal.

2. The system of claim 1, wherein the neurostimulation device is implanted into the central nervous system of the individual for a purpose different from providing the movement cue.

3. The system of claim 2, wherein the neurostimulation device is implanted for deep brain stimulation.

4. The system of claim 2, wherein the neurostimulation device is not being used for the purpose different from providing the movement cue.

5. The system of claim 2, wherein the system further comprises circuitry for operating the neurostimulation device according to the purpose that is different from providing the movement cue.

6. The system of claim 1, wherein the first neuronal stimulation signal comprises a signal designed to be perceived by the individual as periodic.

7. The system of claim 1, wherein the transmitter circuitry is further configured to control one or more of a frequency, a pulse width, a pulse shape or an amplitude of the first neuronal stimulation signal.

8. The system of claim 1, wherein the transmitter circuitry is further configured to control one or more of the movement speed, pace regularity or balance of the individual via the first neuronal stimulation signal.

9. The system of claim 1, wherein the processor is further configured to select the first neuronal stimulation signals to be transmitted to the neurostimulation device.

10. The system of claim 9, wherein the processor is further configured to select a second neuronal stimulation signal of the one more neuronal stimulation signals having a different frequency than the first neuronal stimulation signal for transmission to the neurostimulation device.

11. The system of claim 10, wherein the first neuronal stimulation signal is adapted to control one or more of a movement speed, a pace regularity or a balance of the individual and the second neuronal stimulation signal is adapted to counteract a temporary movement impairment of the individual.

12. The system of claim 1, wherein the transmitter circuitry is further configured to transmit at least two different neuronal stimulation signals to two different contacts of the neurostimulation device at substantially the same time.

13. The system of claim 1, wherein the periodic movement cue comprises a conscious sensory percept in the sensory cortex of the individual.

14. The system of claim 1, further comprising:

one or more sensors configured to obtain information about a body posture of the individual;

wherein the processor is configured to determine, based on the obtained information, a second neuronal stimulation signal to be applied to the neurostimulation device of the individual configured to stimulate afferent sensory neurons of the central nervous system of the individual, wherein the second neuronal stimulation signal corresponds to proprioceptive information to be communicated to the individual; and wherein the transmitter circuitry is further configured to transmit the second neuronal stimulation signal to the neurostimulation device together with the first neuronal stimulation signal.

15. The system of claim 14, wherein the information about the body posture of the individual comprises at least one of:

a. information about an articulation state of a joint of the individual;

b. information about the balance of the body of the individual; and c. information about a surface contact of a part of the body of the individual.

16. The system of claim 14, wherein the processor is further configured to access relations stored on the non-transitory memory, wherein the relations are specific for the individual, wherein the relations comprise relations between a plurality of proprioceptive information and a plurality of corresponding neuronal stimulation signals.

17. The system of claim 16, wherein the relations are based at least in part on proprioceptive learning data for the individual, wherein the learning data associates the plurality of proprioceptive information with the plurality of corresponding neuronal stimulation signals.

18. The system of claim 14, wherein the proprioceptive information is related to a body part of the individual involved in a movement of the individual associated with the movement information.

19. The system of claim 14, wherein the transmitter circuitry is adapted to control one or more of a frequency, a pulse width, a pulse shape and or an amplitude of one or both of the first and second neuronal stimulation signals.

20. The system of claim 14, wherein the transmitter circuitry is adapted to control a relative timing between the first and the second neuronal stimulation signals.

21. The system of claim 14, wherein the second neuronal stimulation signal is adapted to be provided quasi-continuously with respect to the first neuronal stimulation signal.

22. A non-transitory computer-readable memory medium comprising program instructions which, when executed by a processor, cause an electronic information processing device to:

obtain a first neuronal stimulation signal from one or more neuronal stimulation signals stored on the non-transitory computer-readable memory medium; and cause transmitter circuitry to:
  transmit the first neuronal stimulation signal to a neurostimulation device of the individual configured to stimulate afferent sensory axons of a central nervous system of the individual projecting to the sensory cortex of the individual, wherein the neurostimulation device is further configured to apply a neuromodulation therapy to the central nervous system of the individual, wherein the first neuronal stimulation signal is applied via one or more electric contacts of a neurostimulation electrode of the neurostimulation device that are not used for applying the neuromodulation therapy, and wherein the first neuronal stimulation signal is configured to provide a periodic movement cue to the sensory cortex of the individual; and
  transmit a neuromodulation therapy stimulation signal to the neurostimulation device to apply the neuromodulation therapy via one or more electric contacts of the neurostimulation electrode that are not used for applying the first neuronal stimulation signal.

23. The non-transitory computer-readable memory medium of claim 22, wherein the program instructions are further executable to cause the electronic information processing device to:
  obtain information about a body posture of the individual from one or more sensors;
  determine, based on the obtained information, a second neuronal stimulation signal to be applied to the neurostimulation device of the individual configured to stimulate the afferent sensory neurons of the central nervous system of the individual, wherein the second neuronal stimulation signal corresponds to proprioceptive information to be communicated to the individual; and
  cause the transmitter circuitry to transmit the second neuronal stimulation signal to the neurostimulation device together with the first neuronal stimulation signal.

24. The non-transitory computer-readable memory medium of claim 23, wherein the proprioceptive information is related to a body part of the individual involved in a movement of the individual associated with the movement information.

25. The non-transitory computer-readable memory medium of claim 23, wherein the program instructions are further executable to cause the electronic information processing device to cause the transmitter circuitry to control one or more of a frequency, a pulse width, a pulse shape and or an amplitude of one or both of the first and second neuronal stimulation signals.

26. The non-transitory computer-readable memory medium of claim 23,
  wherein the program instructions are further executable to cause the electronic information processing device to cause the transmitter circuitry to control a relative timing between the first and the second neuronal stimulation signals.

27. The non-transitory computer-readable memory medium of claim 23, wherein the second neuronal stimulation signal is adapted to be provided at a rate that is more than 20 times larger than a frequency of the first neuronal stimulation signal.

28. The non-transitory computer-readable memory medium of claim 23, wherein the second neuronal stimulation signal is adapted to be provided quasi-continuously with respect to the first neuronal stimulation signal.

29. The non-transitory computer-readable memory medium of claim 22, wherein the program instructions are further executable to cause the electronic information processing device to:
  receive user input via a user interface for selecting the first neuronal stimulation signal.

30. A method, comprising:
  by a distributed electronic information processing system:
    obtaining a first neuronal stimulation signal of one or more neuronal stimulation signals stored on non-transitory memory; and
    transmitting, by transmitter circuitry of the distributed electronic information processing system, the first neuronal stimulation signal to a neurostimulation device of the individual configured to stimulate afferent sensory axons of a central nervous system of the individual projecting to the sensory cortex of the individual, wherein the neurostimulation device is further configured to apply a neuromodulation therapy to the central nervous system of the individual, wherein the first neuronal stimulation signal is applied via one or more electric contacts of a neurostimulation electrode of the neurostimulation device that are not used for applying the neuromodulation therapy, and wherein the first neuronal stimulation signal is configured to provide a periodic movement cue to the sensory cortex of the individual; and
    transmitting a neuromodulation therapy stimulation signal to the neurostimulation device to apply the neuromodulation therapy via one or more electric contacts of the neurostimulation electrode that are not used for applying the first neuronal stimulation signal.

31. The method of claim 30, further comprising:
  obtaining information about a body posture of the individual from one or more sensors;
  determining, based on the obtained information, a second neuronal stimulation signal to be applied to the neurostimulation device of the individual configured to stimulate the afferent sensory neurons of the central nervous system of the individual, wherein the second neuronal stimulation signal corresponds to proprioceptive information to be communicated to the individual; and
  transmitting, by the transmitter circuitry, the second neuronal stimulation signal to the neurostimulation device together with the first neuronal stimulation signal.

32. The method of claim 31, wherein the proprioceptive information is related to a body part of the individual involved in a movement of the individual associated with the movement information.

33. The method of claim 31, further comprising:
  controlling one or more of a frequency, a pulse width, a pulse shape and or an amplitude of one or both of the first and second neuronal stimulation signals.

34. The method of claim 31, further comprising:
  controlling a relative timing between the first and the second neuronal stimulation signals.

35. The method of claim 31, wherein the second neuronal stimulation signal is adapted to be provided at a rate that is more than 20 times larger than a frequency of the first neuronal stimulation signal.

36. The method of claim 30, further comprising:
receiving user input via a user interface for selecting the first neurostimulation signal.

\* \* \* \* \*